United States Patent [19]

Boyer et al.

[11] Patent Number: 4,609,733

[45] Date of Patent: Sep. 2, 1986

[54] 3-KETO-SUBSTITUTED-N-PYRIDYLIN-DOLES

[75] Inventors: Stephen K. Boyer, Far Hills; Karl O. Gelotte, Watchung; Joseph Bach, Parsippany, all of N.J.

[73] Assignee: Ciba-Geigy Corporation, Ardsley, N.Y.

[21] Appl. No.: 686,777

[22] Filed: Dec. 27, 1984

[51] Int. Cl.[4] .......................................... C07D 401/04
[52] U.S. Cl. .................................... 546/273; 546/270; 546/256; 514/333; 514/338; 514/339
[58] Field of Search ....................... 546/273, 270, 256; 514/339, 338, 333

[56] References Cited

U.S. PATENT DOCUMENTS

| 3,449,348 | 6/1969 | Shen et al. | 546/273 |
| 3,933,853 | 1/1976 | Demarne | 546/273 |
| 4,322,533 | 3/1982 | Lesher et al. | 546/273 |
| 4,363,912 | 12/1982 | Cross et al. | 546/273 |
| 4,416,895 | 11/1983 | Thorogood | 514/396 |
| 4,451,472 | 5/1984 | Cross et al. | 546/273 |
| 4,460,777 | 7/1984 | Renfroe | 546/273 |
| 4,478,842 | 10/1984 | Renfroe | 546/270 |
| 4,511,573 | 4/1985 | Renfroe | 514/332 |
| 4,536,505 | 8/1985 | Browne | 514/339 |

FOREIGN PATENT DOCUMENTS

| 299938 | 7/1972 | Austria . |
| 323154 | 9/1974 | Austria . |
| 73663 | 3/1983 | European Pat. Off. . |
| 0126401 | 11/1984 | European Pat. Off. . |
| 2171937 | 9/1973 | France . |
| 2102795 | 2/1983 | United Kingdom . |

OTHER PUBLICATIONS

Demarne, Chem. Abst. 33811n, vol. 80, 1974 and Chem. Abst. 59863p, vol. 80, 1974.
Khan et al., J. Chem. Soc. (C), 1970, p. 85.
A. H. Jackson et al., Chemical Communications, 1967, 264–266.
R. O. Hutchins et al—Amine Boranes Review, Organic Preparations and Procedures Int. 16(5), 335–372 (1984).

J. F. Stoddart, editor, Comprehensive Organic Chemistry, 1979, vol. 1, pp. 1079–1081.

Primary Examiner—Jane T. Fan
Attorney, Agent, or Firm—Norbert Gruenfeld

[57] ABSTRACT

Disclosed is a process for the preparation of a compound of the formula

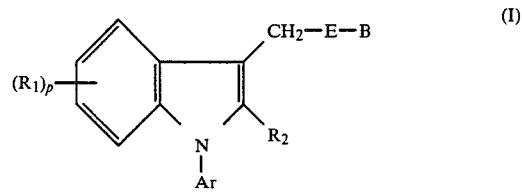

wherein Ar is 3- or 4-pyridyl or 3- or 4-pyridyl substituted by lower alkyl; $R_1$ is hydrogen, halogen, trifluoromethyl, lower alkyl, hydroxy, acylated or etherified hydroxy, lower alkylthio; or two of $R_1$ on adjacent carbon atoms represent alkylenedioxy; p is 1 or 2; $R_2$ represents hydrogen or lower alkyl; E represents $C_1$–$C_{11}$ alkylene, $C_1$–$C_6$ alkylenephenylene, $C_1$–$C_6$ alkylene-(thio or oxy)-lower alkyl, $C_1$–$C_6$ alkylene-(thio or oxy)-phenylene, $C_1$–$C_6$ alkylenephenylene-lower alkylene, phenylene-lower alkylene; or E represents a direct bond; and B represents carboxy, esterified carboxy or carbamoyl; which comprises deoxygenating the keto group in a compound of the formula

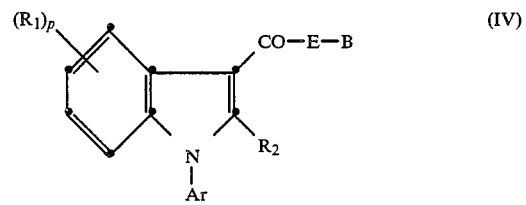

wherein Ar, $R_1$, $R_2$, p, E and B have meaning as defined above.

6 Claims, No Drawings

3-KETO-SUBSTITUTED-N-PYRIDYLINDOLES

The present invention is concerned with a novel process and novel intermediates for the preparation of 3-substituted N-pyridylindoles of the formula I

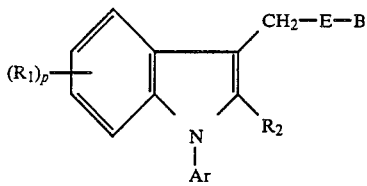

wherein
Ar is 3- or 4-pyridyl or 3- or 4-pyridyl substituted by lower alkyl;
$R_1$ is hydrogen, halogen, trifluoromethyl, lower alkyl, hydroxy, acylated or etherified hydroxy, lower alkylthio; or two of $R_1$ on adjacent carbon atoms represent alkylenedioxy;
p is 1 or 2;
$R_2$ represents hydrogen or lower alkyl;
E represents $C_1$–$C_{11}$ alkylene, $C_1$–$C_6$ alkylene-phenylene, $C_1$–$C_6$ alkylene-(thio or oxy)-lower alkylene, $C_1$–$C_6$ alkylene-(thio or oxy)-phenylene, $C_1$–$C_6$ aklylene-phenylene-lower alkylene, phenylene-lower alkylene; or E represents a direct bond;
B represents carboxy, esterified carboxy or carbamoyl; and pharmaceutically acceptable salts thereof.

The compounds encompassed by formula I are useful as thromboxane synthetane inhibitors and have been disclosed as such in European Patent application No. 126,401, published Nov. 28, 1984, and substantially equivalent to U.S. patent application Ser. No. 495,370 filed May 17, 1983, now U.S. Pat. No. 4,536,505.

A preferred embodiment of this invention relates to the preparation of compounds of formula I wherein Ar is 3-pyridyl; $R_1$ is hydrogen, halogen, trifluoromethyl, lower alkyl, lower alkoxy, lower alkylthio, hydroxy or lower alkanoyloxy; p is 1; $R_2$ represents hydrogen or lower alkyl; E has meaning as defined above; and B represents carboxy, lower alkoxycarbonyl or carbamoyl; and pharmaceutically acceptable salts thereof.

The process of the instant invention is further preferred for the preparation of the compounds of formula I wherein E represents $C_2$–$C_9$ alkylene, phenylene, $C_1$–$C_3$ alkylenephenylene, $C_1$–$C_3$ alkylene-thio-phenylene or $C_1$–$C_3$ alkylene-oxy-phenylene; B represents carboxy or lower alkoxycarbonyl; $R_1$ represents hydrogen, lower alkyl, trifluoromethyl, hydroxy, lower alkylthio or lower alkoxy; p is 1; Ar is 3-pyridyl; $R_2$ represents hydrogen or lower alkyl; and pharmaceutically acceptable salts thereof.

The process of the instant invention is especially useful for the preparation of the compounds of formula I wherein E represents alkylene of 2 to 7 carbon atoms.

A particularly preferred embodiment of the invention is the process of the instant invention for the preparation of the compounds of formula II

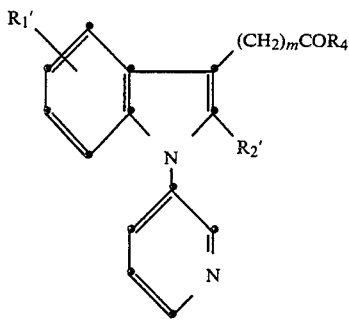

wherein
$R_1'$ represents hydrogen, lower alkyl, halogen, trifluoromethyl, hydroxy, lower alkylthio or lower alkoxy;
$R_2'$ represents hydrogen or lower alkyl;
m represents an interger from 1 to 10; $R_4$ represents hydroxy, lower alkoxy or amino; and pharmaceutically acceptable salts thereof.

More particularly, the process of the instant invention is useful for the preparation of the compounds of formula II wherein $R_1'$ represents hydrogen, methyl, chloro, fluoro, trifluoromethyl, hydroxy, methylthio or methoxy; $R_2'$ represents hydrogen; m represents an integer from 3 to 8; $R_4$ represents hydroxy, ethoxy, methoxy or amino; and pharmaceutically acceptable salts thereof.

The process of the instant invention is particularly useful for the preparation of the compounds of formula II wherein $R_1'$ and $R_2'$ represent hydrogen; m is 3, 4 or 5; $R_4$ represents hydroxy, methoxy or ethoxy; and pharmaceutically acceptable salts thereof.

A further preferred embodiment of the invention is the process of the instant invention for the preparation of the compounds of formula III

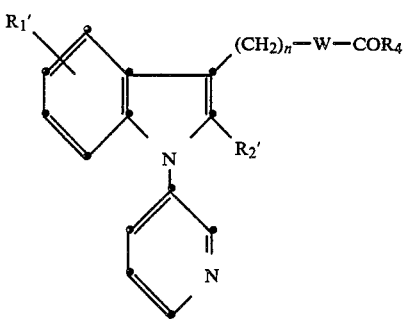

wherein $R_1'$ represents hydrogen, lower alkyl, halogen, trifluoromethyl, hydroxy, lower alkylthio or lower alkoxy; $R_2'$ represents hydrogen or lower alkyl; $R_4$ represents hydroxy, lower alkoxy or amino; n represents an integer from 1 to 4; W represents (thio or oxy)-alkylene of 1 to 4 carbon atoms, (thio or oxy)-1,4-phenylene or 1,4-phenylene; and pharmaceutically acceptable salts thereof.

The general definitions used herein have the following meanings within the scope of the present invention.

The term "$C_1$–$C_{11}$ alkylene" represents straight chain or branched alkylene of 1 to 11 carbon atoms, preferably ethylene, propylene, butylene, pentylene, hexylene, or heptylene, said radicals being unsubstituted or substituted by one or more lower alkyl groups with the proviso that the total number of carbon atoms equals no more than 11.

The term phenylene represents 1,2-, 1,3- and preferably 1,4-phenylene.

The term "lower" when referred to above and hereinafter in connection with organic groups, radicals or compounds respectively defines such with up to and including 7, preferably up to and including 4 and advantageously one, two or three carbon atoms.

A $C_1-C_6$ alkylenephenylene group, a $C_1-C_6$ alkylenephenylene-lower alkylene group, a $C_1-C_6$ aklylene-(thio or oxy)-phenylene group preferably contains 1 to 4 carbon atoms and advantageously one or two carbon atoms in each alkylene portion. The alkylene portions are straight chain or branched.

A $C_1-C_6$ alkylene-(thio or oxy)-lower alkylene group is straight chain or branched and may contain a total of 2 to 11 carbon atoms, preferably 2 to 8 carbon atoms.

A lower alkyl group preferably contains 1–4 carbon atoms and represents for example ethyl, propyl, butyl or advantageously methyl.

A lower alkylene group preferably contains 1–4 carbon atoms and represents for example methylene, ethylene, 1,3-propylene, 1,3- or 1,4-butylene.

A lower alkylenedioxy group represents preferably ethylenedioxy and methylenedioxy.

A lower alkoxy group preferably contains 1–4 carbon atoms and represents for example, ethoxy, propoxy or advantageously methoxy. A lower alkylthio group represents advantageously methylthio.

A lower alkoxycarbonyl group preferably contains 1–4 carbon atoms in the alkoxy portion and represents for example: methoxycarbonyl, propoxycarbonyl, isopropoxycarbonyl or advantageously ethoxycarbonyl.

Halogen is preferably fluorine and chlorine, but may also represent bromine or iodine.

An aryl group, such as in aryl-lower alkoxy represents preferably phenyl, phenyl mono- or di-substituted by lower alkyl, halogen or lower alkoxy, or pyridyl.

An aryl-lower alkoxy group advantageously represents benzyloxy.

Acylated hydroxy represents preferably lower alkanoyloxy e.g. acetyloxy, benzoyloxy, benzoyloxy substituted on the phenyl ring by lower alkyl, halogen or lower alkoxy, e.g. methyl, chloro or methoxy respectively, or nicotinoyloxy.

Etherified hydroxy represents preferably lower alkoxy or aryl-lower alkoxy, e.g. methoxy, benzyloxy, benzyloxy substituted on the phenyl ring by lower alkyl, halogen or lower alkoxy, e.g. methyl, chloro or methoxy respectively, or pyridylmethoxy.

Esterified carboxy represents carboxy esterified preferably in the form of a pharmaceutically acceptable ester, e.g. lower alkoxycarbonyl; (amino, mono- or di-lower alkylamino)-substituted lower alkoxycarbonyl; carboxy-substituted lower alkoxycarbonyl, e.g. α-carboxy-substituted lower alkoxycarbonyl; lower alkoxycarbonyl-substituted lower alkoxycarbonyl, e.g. α-lower alkoxycarbonyl-substituted lower alkoxycarbonyl; aryl-substituted lower alkoxycarbonyl, e.g. optionally substituted benzyloxycarbonyl or pyridylmethoxycarbonyl; (hydroxy, lower alkanoyloxy or lower alkoxy)-substituted lower alkoxycarbonyl, e.g. pivaloyloxymethoxycarbonyl; (hydroxy, lower alkanoyloxy or lower alkoxy)-substituted lower alkoxymethoxycarbonyl; bicycloalkoxycarbonyl-substituted lower alkoxycarbonyl, e.g. bicyclo[2,2,1]-heptyloxycarbonyl-substituted lower alkoxycarbonyl, especially bicyclo[2,2,1-]heptyloxycarbonyl-substituted methoxy such as bornyloxycarbonylmethoxycarbonyl; 3-phthalidoxycarbonyl; (lower alkyl, lower alkoxy, halo)-substituted 3-phthalidoxycarbonyl, lower alkoxycarbonyloxy-lower alkoxycarbonyl, e.g. 1-(methoxy or ethoxycarbonyloxy)ethoxycarbonyl; aryloxycarbonyl, e.g. phenoxycarbonyl or phenoxycarbonyl advantageously substituted at the ortho position by carboxy of lower alkoxycarbonyl.

Pharmaceutically acceptable salts are preferably metal or ammonium salts of said compounds of formula I having a free carboxy group, more particularly alkali or alkaline earth metal salts, e.g., the sodium, potassium, magnesium or calcium salt; or advantageously easily crystallizing ammonium salts derived from ammonia or organic amines, such as mono- di- or tri-lower (alkyl, cycloalkyl or hydroxyalkyl)-amines, lower aklylenediamines or lower (hydroxyalkyl or aralkyl)-alkylammonium hydroxides, e.g., methylamine, diethylamine, triethylamine, dicyclohexylamine, triethanolamine, ethylenediamine, tris-(hydroxymethyl)aminomethane, or benzyltrimethylammonium hydroxide. Said compounds of formula I form acid addition salts of preferably the pharmaceutically acceptable inorganic or organic acids, such as of strong mineral acids, for example hydrohalic, e.g. hydrochloric or hydrobromic acid; sulfuric, phosphoric, nitric or perchloric acid; aliphatic or aromatic carboxylic or sulfonic acids, e.g., acetic, propionic, succinic, glycolic, lactic, malic, tartaric, gluconic, citric, ascorbic, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic or cyclohexylsulfamic acid.

The compounds of formula I, II and III exhibit valuable pharmacological properties, e.g. cardiovascular effects, by selectively decreasing thromboxane levels through selective inhibition of thromboxane synthetase in mammals. The compounds are thus useful for treating diseases responsive to thromboxane synthetase inhibition in mammals, primarily cardiovascular disorders such as thrombosis, atherosclerosis, coronary spasm, cerebral ischaemic attacks, migraine and other vascular headaches, myocardial infarction, angina pectoris, and hypertension.

These effects are demonstrable in in vitro tests or in vivo animal tests using advantageously mammals, e.g. guinea pigs, mice, rats, cats, dogs, or monkeys. Said compounds can be administered to them enterally or parenterally, advantageously orally, or subcutaneously, intravenously or intraperitioneally, for example, within gelatin capsules, or in the form of starchy suspensions or aqueous solutions respectively. The applied dosage may range between about 0.01 to 100 mg/kg/day, preferably between about 0.05 and 50 mg/kg/day, advantageously between about 0.1 and 25 mg/kg/day.

The in vitro inhibition of the thromboxane synthetase enzyme can be demonstrated, analogous to the method of Sun, Biochem. Biophys. Res. Comm. 74, 1432 (1977). The testing procedure is essentially carried out as described in U.S. Pat. No. 4,460,777.

The in-vitro effect on prostaglandin cyclooxygenase is measured by a modification of the method of Takeguchi et al. described in Biochemistry 10, 2372 (1971); the testing procedure is described in U.S. Pat. No. 4,460,777.

The in-vitro effect on prostacyclin (PGI$_2$) synthetase is measured analogous to the method of Sun et al., Prostaglandins 14, 1055 (1977). The testing procedure is described in U.S. Pat. No. 4,460,777.

The inhibition of the synthesis and the reduction of plasma levels of thromboxane is determined in vivo on administration to rats (as adapted from the procedures described by Tai et al. in Anal. Biochem. 87:343, 1978 and by Salmon in Prostaglandins 15:383, 1978) using the procedure described in U.S. Pat. No. 4,460,777.

Compounds of the formulae I, II and III are very potent and selective thromboxane synthetase inhibitors. At the effective dose levels for thromboxane synthetase inhibition neither the beneficial prostacyclin synthetase enzyme system nor the prostaglandin cyclooxygenase enzyme system is significantly inhibited. The prostacyclin levels are actually significantly increased.

Illustrative thereof, the IC$_{50}$ for 3-(4-carboxybutyl)-N-(3-pyridyl)indole is about $1.1 \times 10^{-9}$M for thromboxane synthetase inhibition. The IC$_{50}$ for cyclooxygenase inhibition is greater than $1 \times 10^{-3}$M.

Further illustrative thereof, the IC$_{50}$ for thromboxane synthetase inhibition is e.g. about $4.0 \times 10^{-9}$M for 3-(5-carboxypentyl)-N-(3-pyridyl)indole, and about $2.6 \times 10^{-9}$M for 3-(4-carboxybutyl)-5-chloro-N-(3-pyridyl)indole.

3-(4-Carboxybutyl)-N-(3-pyridyl)indole, as a representative illustrative compound, decreases the plasma concentration of thromboxane B$_2$ by over 50% in the rat at an oral dose of 0.04 mg/kg or lower; an approximately 5-fold increase in the plasma level of prostacyclin is observed.

The present invention is concerned with a novel process for the preparation of the above-cited compounds of formulae I, II, III and the novel corresponding starting materials of formulae IV, V and VI respectively.

The novel process for the preparation of the compounds of formula I comprises deoxygenating the keto group in a compound of the formula

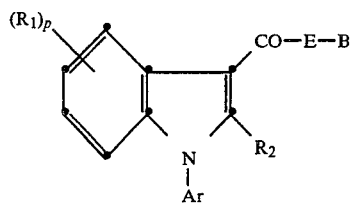

wherein Ar, R$_1$, R$_2$, p, E and B have meaning as defined hereinabove for the compounds of formula I, while, if necessary, temporarily protecting any interfering reactive group(s) and then isolating the resulting compound of formula I; and, if desired, subsequently converting a resulting compound of formula I into another compound of formula I; and, if desired, converting a resulting free compound into a salt or a resulting salt into the free compound or into another salt.

More particularly, the compounds of formula II are prepared by deoxygenating the keto group in a compound of the formula V

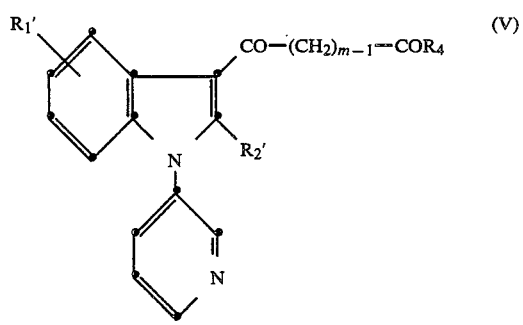

wherein R$_1'$, R$_2'$, m and R$_4$ have meaning as defined hereinabove for the compounds of formula II.

The compounds of formula III are prepared by deoxygenating the keto group in a compound of the formula VI

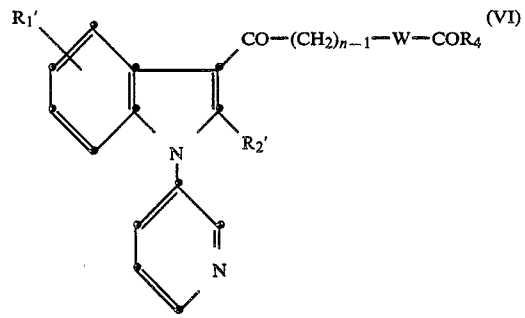

wherein R$_1'$, R$_2'$, R$_4$, n and W have meaning as defined hereinabove for the compounds of formula III.

The preparation of the compounds of formula II or III is carried out while, if necessary, temporarily protecting any interferring reactive group(s) and then isolating the resulting compound of formula II or III; and, if desired, subsequently converting a resulting compound of formula II or III into another compound of formula II or III respectively; and, if desired, converting a resulting free compound into a salt or a resulting salt into a free compound or into another salt.

For the above-cited deoxygenation process in which the carbonyl group directly attached to the indole ring is deoxygenated to methylene, a compound of formula IV, V or VI is treated under reduction conditions selective for the deoxygenation of said carbonyl group to methylene, advantageously leading to little or no reduction of other functional groups present, i.e. the carboxy, esterified carboxy or carboxamide groups.

A preferred reagent to achieve said deoxygenation is borane in form of a amine complex, such as with an aliphatic, aromatic, or cyclic amine, e.g. with t-butylamine, pyridine, N,N-diethylaniline, diisopropylamine, 4-dimethylaminopyridine, dimethylamine, 4-methylmorpholine or the like, preferably under acidic conditions.

The deoxygenation with the borane-amine complex is carried out preferably in an acidic polar solvent, advantageously a lower alkylcarboxylic acid, e.g. acetic acid, with or without an additional inert solvent, or in an inert solvent such as toluene, tetrahydrofuran or diglyme in the presence of a Lewis acid such as aluminum chloride or stannic chloride, at a temperature ranging from about 0° to 100°, advantageously at or near room temperature.

The deoxygenation of the carbonyl group according to the process of the instant invention may also be carried out using other carbonyl deoxygenation methods known in the art, e.g. such as described in Comprehensive Organic Chemistry vol. 1, edited by I. F. Stoddart, pages 1079–1081. Applicable methods comprise: catalytic hydrogenation; Clemmensen reduction, e.g. with zinc amalgam or tin under acidic conditions; reduction of a hydrazone derivative of the carbonyl function, e.g. a tosylhydrazone derivative with sodium cyanoborohydride; reductive desulfurization of a thioketal derivative, e.g. of the ethylenedithio derivative with Raney nickel or tributyl tin hydride in the presence of azobis(isobutyronitrile).

The novel intermediates of formula IV (and V or VI) are prepared by acylating, preferably under acidic catalysis, a compound of the formula VII

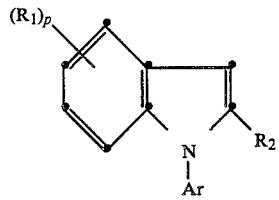

(VII)

wherein Ar, $R_1$, $R_2$ and p have meaning as defined hereinabove for the compounds of formula I, with a compound of formula VIII

HOOC—E—B       (VIII)

wherein E and B have meaning as defined hereinabove, or preferably a reactive functional derivative thereof.

The starting materials corresponding to formula V and VI are accordingly prepared by acylating, under conditions identical to those defined above, a compound of the formula

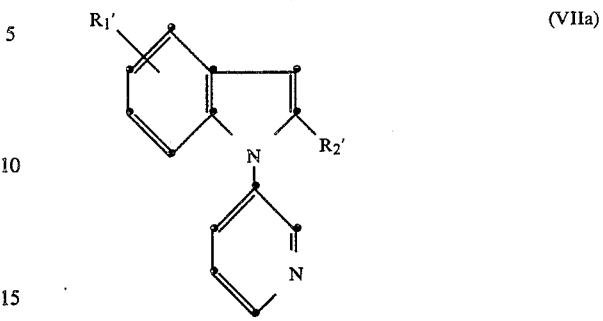

(VIIa)

wherein $R_1'$ and $R_2'$ have meaning as defined above, with a compound of formula VIIIa or VIIIb respectively

HOOC—$(CH_2)_{m-1}$—$COR_4$       (VIIIa)

HOOC—$(CH_2)_{n-1}$—W—$COR_4$       (VIIIb)

wherein m, n, $R_4$ and W have meaning as defined hereinabove, or a reactive functional derivative thereof.

A reactive functional derivative of the carboxylic acids of formula VIII, VIIIa or VIIIb comprises e.g. an acyl halide such as the acid chloride, a simple anhydride in case where B or $COR_4$ represents carboxy, a mixed anhydride, e.g. such derived from a lower alkyl halocarbonate such as ethyl chloroformate and the like known in the art.

The condensation of the indole of formula VII or VIIa with a free carboxylic acid of formula VIII, VIIIa or VIIIb is carried out e.g. in the presence of polyphosphoric acid or polyphosphate ester in an inert solvent such as chloroform, ethylene dichloride, preferably at elevated temperature.

The condensation of an indole of formula VII or VIIa with a reactive functional derivative of a carboxylic acid of formula VIII, VIIIa or VIIIb, e.g. the acid chloride, is carried out in the presence of a Lewis acid, e.g. tin tetrachloride, titanium tetrachloride, boron trifluoride etherate in a polar solvent such as methylene chloride at room or elevated temperature, advantageously at room temperature.

The starting materials of formula VII and formula VIIa are either known in the art (e.g. J. Chem. Soc. (C) 1970, 85) or are prepared analogously from the correspondingly optionally substituted indoles.

The starting materials of formula VIII, VIIIa or VIIIb and functional derivatives thereof are also either known in the art or are prepared by methods well known in the art.

The intermediates of formula IV, V and VI are also useful as thromboxane synthetase inhibitors as determined using methods known in the art, e.g. as cited above and described in U.S. Pat. No. 4,460,777. Illustrative thereof the compound of Example 2 has an $IC_{50}$ of about $4 \times 10^{-7}$M in vitro.

The compounds of formula I, II and III, and intermediates of formula IV, V and VI form acid addition salts, and metal or ammonium salts when B or COR₄ represents carboxy. Acceptable salts are preferably pharmaceutically acceptable salts as described above.

The above-mentioned reactions are carried out according to standard methods, in the presence or absence of diluents, preferably such as are inert to the reagents and are solvents thereof, of catalysts, condensing or said other agents respectively and/or inert atmospheres, at low temperature, room temperature or elevated temperature, preferably near the boiling point of the solvents used, at atmospheric or superatomospheric pressure.

The invention further includes any variant of the present processes, in which an intermediate product obtainable at any state thereof is used as starting meterial and the remaining steps are carried out, or the process is discontinued at any stage thereof, or in which the starting materials are formed under the reaction conditions or in which the reaction components are used in the form of their salts. Whenever desirable, the above processes are carried out after first suitably protecting any potentially interfering reactive functional groups by methods generally known in the art.

In starting compounds and intermediates therefor which are converted to the final compounds in a manner described herein, functional groups present, such as carboxy and hydroxy, are optionally protected by conventional protecting groups that are common in preparative organic chemistry. Protective carboxy and hydroxy groups are those that can be converted under mild conditions into free carboxy and hydroxy groups without the molecular framework being destroyed or other undesired side reactions taking place.

Well-known protecting groups that meet these conditions, their introduction and removal are described, for example, in J. F. W. McOmie, "Protective Groups in Organic Chemistry", Plenum Press, London, New York 1973, T. W. Greene, "Protective Groups in Organic Synthesis", Wiley, New York 1984, and also in Houben-Weyl, "Methoden der Organischen Chemie", Vol. 15/1, George Thieme Verlag, Stuttgart, 1974.

Advantageously, those starting materials should be used in said reactions that lead to the formation of those compounds indicated above as being preferred.

In case mixtures of the above compounds or intermediates are obtained, these can be separated into the single isomers by methods in themselves knnwon, e.g. by fractional distillation, crystallization or chromatography.

Racemic products and intermediates can be resolved into the optical antipodes, for example, by separation of diasteromeric salts thereof, e.g., by the fractional crystallization of d- or l-(tartrate, dibenzoyltartrate, mandelate or camphorsulfonate) salts.

Racemic products or racemic acidic intermediates can also be resolved by separation of e.g. the d- and l-(α-methylbenzylamine, cinchonidine, cinchonine, quinine, quinidine, ephedrine, dehydroabietylamine, brucine or strychnine)-salts of such compounds having an acidic salt-forming group.

The compounds are either obtained in the free form, or as a salt thereof. In view of the close relationship between the free compounds and the compounds in the form of their salts, whenever a compound is referred to in this context, a corresponding salt is also intended, provided such is possible or appropriate under the circumstances.

Any resulting free compound can be converted into a corresponding acid addition salt, preferably with the use of a pharmaceutically acceptable acid or anion exchange preparation. The resulting acid-addition salts can be converted into the corresponding free compounds, for example, with the use of one molar equivalent of a base, such as a metal or ammonium hydroxide or a basic salt, e.g. an alkali metal hydroxide or carbonate, or a cation exchange preparation. Free carboxylic acids can also be converted into the corresponding metal or ammonium salts. These or other salts can also be used for purification of the compounds obtained; the salts are separated and the free compounds are liberated from the salts.

The compounds, including their salts, may also be obtained in the form of their hydrates, or include other solvents used for crystallization.

The compounds of formula I prepared by the process of the instant invention correspond to compounds described e.g. in European Patent Application No. 126,401; their identity is determined by comparison of e.g. melting point, migration on thin layer chromatography, migration on high pressure liquid chromatography and spectral methods such as infrared and nuclear magnetic resonance spectroscopy.

The following examples are intended to illustrate the invention and are not to be construed as being limitations thereon. Temperatures are given in degrees Centigrade. If not mentioned otherwise, all evaporations are performed under reduced pressure preferably between about 15 and 100 mm Hg.

EXAMPLE 1

(a)

To a mixture of 10.0 g of N-(3-pyridyl)-indole (J. Chem. Soc. (C), 85, 1970) and 13.8 g of glutaric acid monoethyl ester chloride in 90 ml of methylene chloride is added dropwise over a period of 3 hours a solution of 20.1 g of stannic chloride in 60 ml of methylene chloride. The reaction mixture is stirred at room temperative overnight. The reaction mixture is cooled to 10°–15° and 150 ml of 14% aqueous ammonium hydroxide is added. The organic layer is separated, washed with water and dried over sodium sulfate to yield 3-(1-oxo-4-ethoxycarbonylbutyl)-N-(3-pyridyl)indole, melting at 95°–97°.

Similarly prepared are:

(b)

3-(1-oxo-2-ethoxycarbonylethyl)-N-(3-pyridyl)-indole;

(c)

3-(1-oxo-3-ethoxycarbonylpropyl)-N-(3-pyridyl)-indole;

(d)

5-bromo-3-(1-oxo-4-ethocycarbonylbutyl)-N-(3-pyridyl)-indole;

(e)

3-(1-oxo-4-ethoxycarbonylbutyl)-2-methyl-N-(3-pyridyl)-indole;

(f)

3-(1-oxo-4-methoxycarbonylbutyl)-7-methyl-N-(3-pyridyl)-indole;

(g)

3-(1-oxo-4-ethoxycarbonylbutyl)-5-methoxy-N-(3-pyridyl)-indole;

(h)

3-(1-oxo-4-ethoxycarbonylbutyl)-5-chloro-N-(3-pyridyl)-indole;

(i)

3-(1-oxo-4-methoxycarbonylbutyl)-5-methyl-N-(3-pyridyl)-indole;

(j)

3-(1-oxo-5-methoxycarbonylpentyl)-N-(3-pyridyl)-indole;

(k)

3-(1-oxo-4-ethoxycarbonylbutyl)-6-chloro-N-(3-pyridyl)-indole.

The ring substituted N-(3-pyridyl)-indole starting materials corresponding to the above products are prepared from the corresponding N-unsubstituted indoles according to J. Chem. Soc. (C), 85 (1970).

EXAMPLE 2

A mixture of 15.0 g of 3-(1-oxo-4-ethoxycarbonylbutyl)-N-(3-pyridyl)indole, 100 ml of 0.5N sodium hydroxide is heated under reflux for 16 hours. The solution is acidified to pH of about 6 with hydrochloric and extracted with methylene chloride. The methylene chloride extract is dried over sodium sulfate and evaporated to dryness to give 3-(1-oxo-4-carboxybutyl)-N-(3-pyridyl)-indole, melting point 177°–178°.

3-(1-Oxo-4-carboxylbutyl)-N-(3-pyridyl)indole can also be prepared by treatment of N-(3-pyridyl)indole with glutaric anhydride in the presence of stannic chloride.

Similarly prepared are the oxo-carboxylic acids of formula V (wherein $R_4$ represents hydroxy) corresponding to the esters (b) through (k) of Example 1.

EXAMPLE 3

(a)

To a solution of 5 g of 3-(1-oxo-4-ethoxycarbonylbutyl)-N-(3-pyridyl)indole in 75 ml of glacial acetic acid is added 5 g of borane-tert-butylamine complex. The reaction mixture is stirred at room temperature overnight. The reaction mixture is concentrated, water is added to the residue and the product is extracted with methylene chloride. The organic layer is separated, washed first with concentrated sodium carbonate solution, then with saturated sodium chloride solution, dried over sodium sulfate and evaporated to dryness to yield 3-(4-ethoxycarbonylbutyl)-N-(3-pyridyl)-indole, melting at 56°–58°.

(b)

A suspension of 0.46 g of 3-(4-ethoxycarbonylbutyl)-N-(3-pyridyl)-indole in 85 ml of aqueous 1N sodium hydroxide solution is heated at 95° for 8 hours. The resulting solution is neutralized with hydrochloric acid to pH of about 5.5. The resulting precipitate is filtered off, and triturated with acetonitrile to yield 3-(4-carboxybutyl)-N-(3-pyridyl)-indole (European Patent Application No. 126,401). 3-(4-Carboxybutyl)-N-(3-pyridyl)-indole has melting point of 122°–124°.

EXAMPLE 4

To a solution of 0.5 g of 3-(1-oxo-4-ethoxycarbonylbutyl)-N-(3-pyridyl)-indole in 25 ml of tetrahydrofuran is added 0.6 g of borane-tert-butylamine complex and 0.6 ml of glacial acetic acid. The reaction mixture is heated at 90° and monitored by high pressure liquid chromatography. When complete, the reaction mixture is evaporated under reduced pressure, water and methylene chloride are added, the pH is adjusted to 7–8 with sodium carbonate solution, the organic layer is separated, washed with water, dried and evaporated to dryness to yield 3-(4-ethoxycarbonylbutyl)-N-(3-pyridyl)-indole.

EXAMPLE 5

Mossy zinc (3.1 g) is treated with a mixture of 0.31 g of mercuric chloride, 0.15 ml of concentrated hydrochloric acid and 4 ml of water for 5 minutes; the solution is then decanted, 7.5 ml of water and 17.5 ml of concentrated hydrochloric acid and 10 ml of toluene are added, followed by 1 g of 3-(1-oxo-4-ethoxycarbonylbutyl)-N-(3-pyridyl)-indole. The reaction mixture is heated under reflux for 24 hours. The reaction mixture is adjusted to pH 6 with 1N sodium hydroxide and extracted with methylene chloride. The methylene chloride solution is washed with water, dried over sodium sulfate and evaporated to dryness to give 3-(4-carboxybutyl)-N-(3-pyridyl)-indole.

EXAMPLE 6

To a solution of 0.5 g of 3-(1-oxo-4-carboxybutyl)-N-(3-pyridyl)-indole in 7.5 ml of glacial acetic acid is added 0.5 g of borane-tert-butylamine complex. The reaction mixture is stirred at room temperature overnight. The reaction mixture is concentrated, the residue is dissolved in 10 ml of 1N sodium hydroxide, water is added to the residue, the pH is adjusted to 5.0 with hydrochloric acid and the product is filtered off and dried to yield 3-(4-carboxybutyl)-N-(3-pyridyl)-indole identical to the compound obtained in Example 3b.

EXAMPLE 7

To a solution of 0.5 g of 3-(1-oxo-4-ethoxycarbonylbutyl)-N-(3-pyridyl)-indole in 15 ml of methylene chloride are added first 0.40 g of aluminum chloride and subsequently 0.175 g of dimethylamine borane complex. The reaction mixture is stirred at room temperature for 24 hours. The mixture is cooled to 0° and 10 ml of water are added dropwise. After ten minutes, 35 ml of 1N aqueous sodium hydroxide are added to adjust pH to 8. The methylene chloride layer is separated, the aqueous layer is further extracted with methylene chloride; the methylene chloride extracts are combined, washed with water, dried and evaporated to dryness to yield 3-(4-ethoxycarbonylbutyl)N-(3-pyridyl)-indole. Hydrolysis with dilute sodium hydroxide yields 3-(4-carboxybutyl)-N-(3-pyridyl)-indole.

EXAMPLE 8

Preparation by deoxygenation methods analogous to those described in the previous examples of the following compounds of formula II wherein $R_4$ represents hydroxy or ethoxy:

| Compound | $R_1'$ | $R_2'$ | m |
|---|---|---|---|
| 1 | H | H | 2 |
| 2 | H | H | 3 |
| 3 | 5-bromo | H | 4 |
| 4 | H | $CH_3$ | 4 |
| 5 | 7-methyl | H | 4 |
| 6 | 5-methoxy | H | 4 |
| 7 | 5-chloro | H | 4 |
| 8 | 5-methyl | H | 4 |
| 9 | H | H | 5 |
| 10 | 6-chloro | H | 4 |

What is claimed is:
1. A compound of the formula

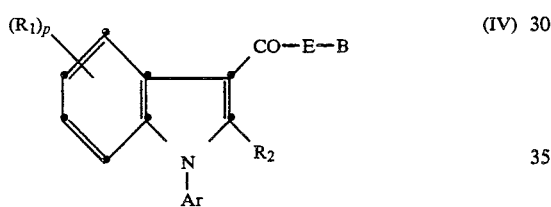

wherein
Ar is 3- or 4-pyridyl or 3- or 4-pyridyl substituted by lower alkyl;
$R_1$ is hydrogen, halogen, trifluoromethyl, lower alkyl, hydroxy, acylated or etherified hydroxy, lower alkylthio; or two of $R_1$ on adjacent carbon atoms represent ethylenedioxy or methylenedioxy; p is 1 or 2;
$R_2$ represents hydrogen or lower alkyl;
E represents $C_1$–$C_{11}$ alkylene, $C_1$–$C_6$ alkylenephenylene, $C_1$–$C_6$ alkylene-(thio or oxy)-lower alkylene, $C_1$–$C_6$ alkylene-(thio or oxy)-phenylene, $C_1$–$C_6$-alkylenephenylene-lower alkylene, phenylene-lower alkylene; or E represents a direct bond;
B represents carboxy, esterified carboxy or carbamoyl; and wherein within the above definitions acylated hydroxy represents lower alkanoyloxy, benzoyloxy, benzoyloxy substituted on phenyl ring by lower alkyl, halogen or lower alkoxy, or nicotinoyloxy; etherified hydroxy represents lower alkoxy, benzyloxy, benzyloxy substituted on the phenyl ring by lower alkyl, halogen or lower alkoxy, or pyridylmethoxy; and esterified carboxy represents carboxy esterified in the form of a pharmaceutically acceptable ester; or a pharmaceutically acceptable salt thereof.

2. A compound according to claim 1 of the formula

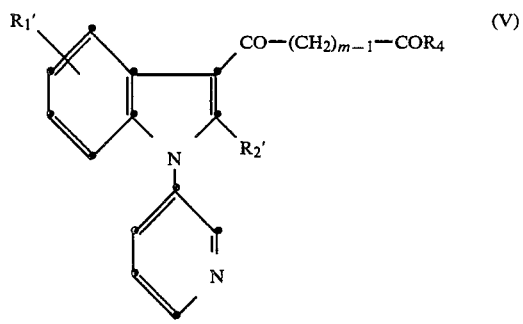

wherein
$R_1'$ represents hydrogen, lower alkyl, halogen, trifluoromethyl, hydroxy, lower alkylthio or lower alkoxy;
$R_2'$ represents hydrogen or lower alkyl;
m represents an interger from 1 to 10; $R_4$ represents hydroxy, lower alkoxy or amino; or a pharmaceutically acceptable salt thereof.

3. A compound according to claim 1 of the formula

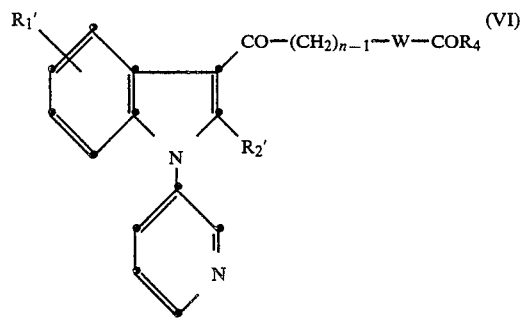

wherein $R_1'$ represents hydrogen, lower alkyl, halogen, trifluoromethyl, hydroxy, lower alkylthio or lower alkoxy; $R_2'$ represents hydrogen or lower alkyl; $R_4$ represents hydroxy, lower alkoxy or amino; n represents an interger from 1 to 4; W represents (thio or oxy)-alkylene of 1 to 4 carbon atoms, (thio or oxy)-1,4-phenylene or 1,4-phenylene; or a pharmaceutically acceptable salt thereof.

4. A compound according to claim 2 wherein $R_1'$ and $R_2'$ represent hydrogen; m is 3, 4 or 5; $R_4$ represents hydroxy, methoxy or ethoxy; or a pharmaceutically acceptable salt thereof.

5. A compound according to claim 2 being 3-(1-oxo-4-ethoxycarbonylbutyl)-N-(3-pyridyl)indole; or a pharmaceutically acceptable salt thereof.

6. A compound according to claim 2 being 3-(1-oxo-4-carboxybutyl-N-(3-pyridyl)indole; or a pharmaceutically acceptable salt thereof.

* * * * *